United States Patent [19]
Kojima et al.

[11] Patent Number: 5,763,236
[45] Date of Patent: Jun. 9, 1998

[54] **METHOD FOR PRODUCING KETONE OR ALDEHYDE USING AN ALCOHOL DEHYDROGENASE OF *CANDIDA PARAPSILOSIS***

[75] Inventors: Tomoko Kojima; Hiroaki Yamamoto; Naoki Kawada, all of Tsukuba; Akinobu Matsuyama, Arai, all of Japan

[73] Assignee: Daicel Chemical Industries Ltd., Sakai, Japan

[21] Appl. No.: 713,254

[22] Filed: Sep. 12, 1996

Related U.S. Application Data

[62] Division of Ser. No. 311,328, Sep. 23, 1994.

[30] Foreign Application Priority Data

| Sep. 24, 1993 | [JP] | Japan | 5-261649 |
| Dec. 28, 1993 | [JP] | Japan | 5-337191 |
| Aug. 2, 1994 | [JP] | Japan | 6-181308 |

[51] Int. Cl.$^6$ .............. C12P 7/16; C12P 7/26; C12N 9/04; C12N 15/53
[52] U.S. Cl. ............ 435/148; 435/147; 435/155; 435/157; 435/160; 435/174; 435/189; 435/190; 435/252.3; 435/254.11; 435/254.22; 536/23.2
[58] Field of Search ............... 435/147, 148, 435/155, 157, 160, 174, 180, 190, 252.3, 254.11, 254.22; 536/23.2

[56] References Cited

U.S. PATENT DOCUMENTS

| 5,200,335 | 4/1993 | Hummel et al. | 435/190 |
| 5,342,767 | 8/1994 | Wong et al. | 435/122 |

FOREIGN PATENT DOCUMENTS

| 1211728 | 9/1986 | Canada . |
| 4009676 | 9/1993 | Germany . |
| 51-57782 | 5/1976 | Japan . |
| 59-17982 | 1/1984 | Japan . |
| WO 93-18138 | 9/1993 | WIPO . |

OTHER PUBLICATIONS

Gwynne, D. I., et al., Gene, vol. 51, "Comparison of the cis–acting regions of two coordinately controlled genes involved in ethanol utilization in *Aspergillus nidulans*", pp. 205–216, 1987.

Shain, D. H., et al., Molecular and General Genetics, vol. 232, "Evolution of the alcohol dehydrogenase (ADH) genes in yeast: characterization of a fourth ADH in *Kluyveromyces lactis*", pp. 479–488, 1992.

Ladriere, J.-M., Biochimica et Biophysica Acta, vol. 1173, "Sequences of a gene coding for a cytoplasmic alcohol dehydrogenase from *Kluyveromyces marxianus* ATCC 12424", pp. 99–101, 1993.

Il'Chenko, A. P., et al., Biokhimiya, vol. 59, "Purification and some properties of alcohol oxidase from the yeast *Yarrowia lipolytica* H–222", pp. 1312–1319, 1994.

Hommel, R. K., et al., Applied Microbiology and Biotechnology, vol. 40, "The inducible microsomal fatty alcohol oxidase of *Candida (Torulopsis) apicola*", pp. 729–734, 1994.

(List continued on next page.)

*Primary Examiner*—Robert A. Wax
*Assistant Examiner*—William W. Moore
*Attorney, Agent, or Firm*—Oblon, Spivak, McClelland, Maier & Neustadt, P.C.

[57] ABSTRACT

The present invention provides a novel secondary alcohol dehydrogenase useful for the synthesis of optically active alcohol and DNA encoding said enzyme. A microorganism belonging to genus Candida was found to produce a novel secondary alcohol dehydrogenase with a high stereochemical specificity. Using said enzyme, optically active alcohols were prepared, and by cloning of DNA encoding said enzyme, the base sequence of said DNA was determined. By providing a novel secondary alcohol dehydrogenase with a high stereochemical specificity and the gene encoding said enzyme, an efficient production of optically active alcohols became possible.

8 Claims, 8 Drawing Sheets

OTHER PUBLICATIONS

Clark, D.S., et al., Bioorganic & Medicinal Chemistry Letters, vol. 4, "Enantioselective oxidation of 2-methyl-1-butanol by alcohol oxidase from methylotropic yeasts", pp. 1745–1748, 1994.

Journal of Biological Chemistry, vol. 268, No. 11, pp. 7792–7798, Apr. 15, 1993, David W. Green, et al., "Inversion of the Substrate Specificity of Yeast Alcohol Dehydrogenase".

Journal of Organic Chemistry, vol. 57, No. 5, pp. 1526–1566, Feb. 28, 1992, Curt W. Bradshaw, et al., "A Pseudomonas sp. Alcohol Dehydrogenase with Broad Substrate Specificity and Unusual Stereospecificity for Organic Synthesis".

```
         10        20        30        40        50        60
ATGTCAATTCCATCAAGCCAGTACGGATTCGTATTCAATAAGCAATCAGGACTTAATCTG
MetSerIleProSerSerGlnTyrGlyPheValPheAsnLysGlnSerGlyLeuAsnLeu
                  CpN
            ─────────────────────►

70        80        90       100       110       120
AGAAATGATTTGCCTGTCCACAAGCCCAAAGCGGGTCAATTGTTGTTGAAAGTTGATGCT
ArgAsnAspLeuProValHisLysProLysAlaGlyGlnLeuLeuLeuLysValAspAla
                      CPA-MUN
            ◄─────────────────────

130       140       150       160       170       180
GTTGGATTGTGTCATTCTGATTTACATGTCATTTACGAAGGGTTGGATTGTGGTGATAAT
ValGlyLeuCysHisSerAspLeuHisValIleTyrGluGlyLeuAspCysGlyAspAsn 190       200       210       220       230       240
TATGTCATGGGACATGAAATTGCTGGAACTGTTGCTGCTGTGGGTGATGATGTCATTAAC
TyrValMetGlyHisGluIleAlaGlyThrValAlaAlaValGlyAspAspValIleAsn 250       260       270       280       290       300
TACAAGGTTGGTGATCGTGTTGCCTGTGTCGGACCCAATGGATGTGGTGGGTGCAAGTAT
TyrLysValGlyAspArgValAlaCysValGlyProAsnGlyCysGlyGlyCysLysTyr 310       320       330       340       350       360
TGTCGTGGTGCCATTGACAATGTATGTAAAAACGCATTTGGTGATTGGTTCGGATTGGGG
CysArgGlyAlaIleAspAsnValCysLysAsnAlaPheGlyAspTrpPheGlyLeuGly
```

*FIG. 6*

```
      370        380        390        400        410        420
TACGATGGTGGGTATCAACAGTACTTGTTGGTTACTAGACCACGTAACTTGTCTCGTATC
TyrAspGlyGlyTyrGlnGlnTyrLeuLeuValThrArgProArgAsnLeuSerArgIle 430        440        450        460        470        480
CCAGATAACGTATCTGCAGACGTGGCTGCGGCTTCAACTGATGCTGTATTGACACCATAT
ProAspAsnValSerAlaAspValAlaAlaAlaSerThrAspAlaValLeuThrProTyr 490        500        510        520        530        540
CACGCAATCAAGATGGCTCAAGTGTCACCAACTTCGAATATCTTGCTTATTGGTGCTGGT
HisAlaIleLysMetAlaGlnValSerProThrSerAsnIleLeuLeuIleGlyAlaGly 550        560        570        580        590        600
GGATTGGGTGGAAATGCAATTCAAGTTGCCAAGGCATTTGGTGCGAAAGTTACTGTTTTG
GlyLeuGlyGlyAsnAlaIleGlnValAlaLysAlaPheGlyAlaLysValThrValLeu 610        620        630        640        650        660
GACAAAAAAAAGGAGGCTCGTGACCAAGCAAAGAAGTTGGGTGCTGATGCAGTTTATGAA
AspLysLysLysGluAlaArgAspGlnAlaLysLysLeuGlyAlaAspAlaValTyrGlu 670        680        690        700        710        720
ACATTGCCAGAATCCATTTCTCCTGGCTCTTTTTCAGCATGTTTTGATTTTGTTTCAGTG
ThrLeuProGluSerIleSerProGlySerPheSerAlaCysPheAspPheValSerVal 730        740        750        760        770        780
CAAGCTACATTTGATGTATGTCAAAAGTATGTTGAACCAAAGGGTGTAATTATGCCCGTG
GlnAlaThrPheAspValCysGlnLysTyrValGluProLysGlyValIleMetProVal
```

*FIG. 7*

```
          790       800       810       820       830       840
GGACTCGGTGCTCCTAATTTATCGTTTAATTTGGGAGATTTGGCATTGAGAGAAATTCGA
Gl yLeuGl yAl aProAsnLeuSerPheAsnLeuGl yAspLeuAl aLeuArgGl uIl eArg
```

```
          850       860       870       880       890       900
ATCTTGGGTAGTTTTTGGGGAACTACTAATGATTTGGATGATGTTTTGAAATTGGTTAGT
Il eLeuGl ySerPheTrpGl yThrThrAsnAspLeuAspAspVal LeuLysLeuVal Ser
    CPA-NSP
    ——————————▶
```

```
          910       920       930       940       950       960
GAAGGTAAAGTTAAACCCGTTGTGAGAAGTGCCAAATTGAAGGAATTGCCAGAGTATATT
Gl uGl yLysVal LysProVal Val ArgSerAl aLysLeuLysGl uLeuProGl uTyrIl e
```

```
          970       980       990       1000      1010
GAAAAATTGAGAAACAATGCTTATGAAGGTAGAGTTGTTTTTAATCCATAG
Gl uLysLeuArgAsnAsnAl aTyrGl uGl yArgVal Val PheAsnPro***
            ◀—————————— CpT10
```

*FIG. 8*

(CpN)

AMINO ACID
SEQUENCE       :   Tyr-Gly-Phe-Val-Phe-Asn-Lys-Gln

DNA SEQUENCE :  5' TAT-GGT-TTT-GTT-TTT-AAT-AAA-CA  3'
(CpN)
                     C   C   C   C   C   C   G

(CpT10)

AMINO ACID
SEQUENCE       :   Asn-Asn-Ala-Tyr-Glu-Gly-Arg

DNA SEQUENCE :  5' AAT-AAT-GCT-TAT-GAA-GGT-CG  3'
                     C   C   C   C   G   C A

COMPLEMENTARY
SEQUENCE       :  3' TTA-TTA-CGA-ATA-CTT-CCA-GC  5'
(Cpt10)
                     G   G   G   G   C   G T

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1011 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Candida parapsilosis ( i x ) FEATURE:
( A ) NAME/KEY: CDS
( B ) LOCATION: 1..1008

( x i ) SEQUENCE DESCRIPTION: SEQ ID NO:1:

```
ATG TCA ATT CCA TCA AGC CAG TAC GGA TTC GTA TTC AAT AAG CAA TCA    48
Met Ser Ile Pro Ser Ser Gln Tyr Gly Phe Val Phe Asn Lys Gln Ser
 1               5                  10                  15

GGA CTT AAT CTG AGA AAT GAT TTG CCT GTC CAC AAG CCC AAA GCG GGT    96
Gly Leu Asn Leu Arg Asn Asp Leu Pro Val His Lys Pro Lys Ala Gly
             20                  25                  30

CAA TTG TTG TTG AAA GTT GAT GCT GTT GGA TTG TGT CAT TCT GAT TTA   144
Gln Leu Leu Leu Lys Val Asp Ala Val Gly Leu Cys His Ser Asp Leu
         35                  40                  45

CAT GTC ATT TAC GAA GGG TTG GAT TGT GGT GAT AAT TAT GTC ATG GGA   192
His Val Ile Tyr Glu Gly Leu Asp Cys Gly Asp Asn Tyr Val Met Gly
     50                  55                  60

CAT GAA ATT GCT GGA ACT GTT GCT GCT GTG GGT GAT GAT GTC ATT AAC   240
His Glu Ile Ala Gly Thr Val Ala Ala Val Gly Asp Asp Val Ile Asn
 65                  70                  75                  80

TAC AAG GTT GGT GAT CGT GTT GCC TGT GTC GGA CCC AAT GGA TGT GGT   288
Tyr Lys Val Gly Asp Arg Val Ala Cys Val Gly Pro Asn Gly Cys Gly
                 85                  90                  95

GGG TGC AAG TAT TGT CGT GGT GCC ATT GAC AAT GTA TGT AAA AAC GCA   336
Gly Cys Lys Tyr Cys Arg Gly Ala Ile Asp Asn Val Cys Lys Asn Ala
            100                 105                 110

TTT GGT GAT TGG TTC GGA TTG GGG TAC GAT GGT GGG TAT CAA CAG TAC   384
Phe Gly Asp Trp Phe Gly Leu Gly Tyr Asp Gly Gly Tyr Gln Gln Tyr
        115                 120                 125

TTG TTG GTT ACT AGA CCA CGT AAC TTG TCT CGT ATC CCA GAT AAC GTA   432
Leu Leu Val Thr Arg Pro Arg Asn Leu Ser Arg Ile Pro Asp Asn Val
    130                 135                 140

TCT GCA GAC GTG GCT GCG GCT TCA ACT GAT GCT GTA TTG ACA CCA TAT   480
Ser Ala Asp Val Ala Ala Ala Ser Thr Asp Ala Val Leu Thr Pro Tyr
145                 150                 155                 160

CAC GCA ATC AAG ATG GCT CAA GTG TCA CCA ACT TCG AAT ATC TTG CTT   528
His Ala Ile Lys Met Ala Gln Val Ser Pro Thr Ser Asn Ile Leu Leu
                165                 170                 175

ATT GGT GCT GGT GGA TTG GGT GGA AAT GCA ATT CAA GTT GCC AAG GCA   576
Ile Gly Ala Gly Gly Leu Gly Gly Asn Ala Ile Gln Val Ala Lys Ala
            180                 185                 190

TTT GGT GCG AAA GTT ACT GTT TTG GAC AAA AAA AAG GAG GCT CGT GAC   624
Phe Gly Ala Lys Val Thr Val Leu Asp Lys Lys Lys Glu Ala Arg Asp
        195                 200                 205

CAA GCA AAG AAG TTG GGT GCT GAT GCA GTT TAT GAA ACA TTG CCA GAA   672
```

```
        Gln  Ala  Lys  Lys  Leu  Gly  Ala  Asp  Ala  Val  Tyr  Glu  Thr  Leu  Pro  Glu
             210                      215                      220

TCC  ATT  TCT  CCT  GGC  TCT  TTT  TCA  GCA  TGT  TTT  GAT  TTT  GTT  TCA  GTG           720
Ser  Ile  Ser  Pro  Gly  Ser  Phe  Ser  Ala  Cys  Phe  Asp  Phe  Val  Ser  Val
225                      230                      235                      240

CAA  GCT  ACA  TTT  GAT  GTA  TGT  CAA  AAG  TAT  GTT  GAA  CCA  AAG  GGT  GTA           768
Gln  Ala  Thr  Phe  Asp  Val  Cys  Gln  Lys  Tyr  Val  Glu  Pro  Lys  Gly  Val
                    245                      250                      255

ATT  ATG  CCC  GTG  GGA  CTC  GGT  GCT  CCT  AAT  TTA  TCG  TTT  AAT  TTG  GGA           816
Ile  Met  Pro  Val  Gly  Leu  Gly  Ala  Pro  Asn  Leu  Ser  Phe  Asn  Leu  Gly
               260                      265                      270

GAT  TTG  GCA  TTG  AGA  GAA  ATT  CGA  ATC  TTG  GGT  AGT  TTT  TGG  GGA  ACT           864
Asp  Leu  Ala  Leu  Arg  Glu  Ile  Arg  Ile  Leu  Gly  Ser  Phe  Trp  Gly  Thr
          275                      280                      285

ACT  AAT  GAT  TTG  GAT  GAT  GTT  TTG  AAA  TTG  GTT  AGT  GAA  GGT  AAA  GTT           912
Thr  Asn  Asp  Leu  Asp  Asp  Val  Leu  Lys  Leu  Val  Ser  Glu  Gly  Lys  Val
     290                      295                      300

AAA  CCC  GTT  GTG  AGA  AGT  GCC  AAA  TTG  AAG  GAA  TTG  CCA  GAG  TAT  ATT           960
Lys  Pro  Val  Val  Arg  Ser  Ala  Lys  Leu  Lys  Glu  Leu  Pro  Glu  Tyr  Ile
305                      310                      315                      320

GAA  AAA  TTG  AGA  AAC  AAT  GCT  TAT  GAA  GGT  AGA  GTT  GTT  TTT  AAT  CCA          1008
Glu  Lys  Leu  Arg  Asn  Asn  Ala  Tyr  Glu  Gly  Arg  Val  Val  Phe  Asn  Pro
                    325                      330                      335

TAG                                                                                      1011
```

( 2 ) INFORMATION FOR SEQ ID NO:2:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Ile  Pro  Ser  Ser  Gln  Tyr  Gly  Phe  Val  Phe  Asn  Lys  Gln  Ser
1                   5                        10                       15

Gly  Leu  Asn  Leu  Arg  Asn  Asp  Leu  Pro  Val  His  Lys  Pro  Lys  Ala  Gly
               20                       25                       30

Gln  Leu  Leu  Leu  Lys  Val  Asp  Ala  Val  Gly  Leu  Cys  His  Ser  Asp  Leu
          35                       40                       45

His  Val  Ile  Tyr  Glu  Gly  Leu  Asp  Cys  Gly  Asp  Asn  Tyr  Val  Met  Gly
     50                       55                       60

His  Glu  Ile  Ala  Gly  Thr  Val  Ala  Ala  Val  Gly  Asp  Asp  Val  Ile  Asn
65                       70                       75                       80

Tyr  Lys  Val  Gly  Asp  Arg  Val  Ala  Cys  Val  Gly  Pro  Asn  Gly  Cys  Gly
                    85                       90                       95

Gly  Cys  Lys  Tyr  Cys  Arg  Gly  Ala  Ile  Asp  Asn  Val  Cys  Lys  Asn  Ala
               100                      105                      110

Phe  Gly  Asp  Trp  Phe  Gly  Leu  Gly  Tyr  Asp  Gly  Gly  Tyr  Gln  Gln  Tyr
          115                      120                      125

Leu  Leu  Val  Thr  Arg  Pro  Arg  Asn  Leu  Ser  Arg  Ile  Pro  Asp  Asn  Val
     130                      135                      140

Ser  Ala  Asp  Val  Ala  Ala  Ala  Ser  Thr  Asp  Ala  Val  Leu  Thr  Pro  Tyr
145                      150                      155                      160

His  Ala  Ile  Lys  Met  Ala  Gln  Val  Ser  Pro  Thr  Ser  Asn  Ile  Leu  Leu
                    165                      170                      175

Ile  Gly  Ala  Gly  Gly  Leu  Gly  Gly  Asn  Ala  Ile  Gln  Val  Ala  Lys  Ala
               180                      185                      190
```

| | | | | | | | | | | | | | |
|---|---|---|---|---|---|---|---|---|---|---|---|---|---|
| Phe | Gly | Ala | Lys | Val | Thr | Val | Leu | Asp | Lys | Lys | Lys | Glu | Ala | Arg | Asp |
| | | 195 | | | | 200 | | | | | 205 | | |
| Gln | Ala | Lys | Lys | Leu | Gly | Ala | Asp | Ala | Val | Tyr | Glu | Thr | Leu | Pro | Glu |
| | 210 | | | | | 215 | | | | | 220 | | |
| Ser | Ile | Ser | Pro | Gly | Ser | Phe | Ser | Ala | Cys | Phe | Asp | Phe | Val | Ser | Val |
| 225 | | | | | 230 | | | | | 235 | | | | | 240 |
| Gln | Ala | Thr | Phe | Asp | Val | Cys | Gln | Lys | Tyr | Val | Glu | Pro | Lys | Gly | Val |
| | | | | 245 | | | | | 250 | | | | | 255 |
| Ile | Met | Pro | Val | Gly | Leu | Gly | Ala | Pro | Asn | Leu | Ser | Phe | Asn | Leu | Gly |
| | | | 260 | | | | | 265 | | | | | 270 | |
| Asp | Leu | Ala | Leu | Arg | Glu | Ile | Arg | Ile | Leu | Gly | Ser | Phe | Trp | Gly | Thr |
| | | 275 | | | | | 280 | | | | | 285 | | |
| Thr | Asn | Asp | Leu | Asp | Asp | Val | Leu | Lys | Leu | Val | Ser | Glu | Gly | Lys | Val |
| | 290 | | | | | 295 | | | | | 300 | | |
| Lys | Pro | Val | Val | Arg | Ser | Ala | Lys | Leu | Lys | Glu | Leu | Pro | Glu | Tyr | Ile |
| 305 | | | | | 310 | | | | | 315 | | | | | 320 |
| Glu | Lys | Leu | Arg | Asn | Asn | Ala | Tyr | Glu | Gly | Arg | Val | Val | Phe | Asn | Pro |
| | | | | 325 | | | | | 330 | | | | | 335 |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

TAYGGNTTYG TNTTYAAYAA RCA            23

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

Tyr Gly Phe Val Phe Asn Lys Gln
1               5

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:5:

CAATTGACCC GCTTTGGGC            19

( 2 ) INFORMATION FOR SEQ ID NO:6:

( i ) SEQUENCE CHARACTERISTICS:
        ( A ) LENGTH: 22 base pairs
        ( B ) TYPE: nucleic acid ( C ) STRANDEDNESS: single
                ( D ) TOPOLOGY: unknown ( i i ) MOLECULE TYPE: DNA (genomic)

( x i ) SEQUENCE DESCRIPTION: SEQ ID NO:6:

TTCGAATCTT GGGTAGTTTT TG								22

( 2 ) INFORMATION FOR SEQ ID NO:7:

( i ) SEQUENCE CHARACTERISTICS:
                ( A ) LENGTH: 20 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:7:

AAYAAYGCNT AYGARGGNMG								20

( 2 ) INFORMATION FOR SEQ ID NO:8:

( i ) SEQUENCE CHARACTERISTICS:
                ( A ) LENGTH: 7 amino acids
                ( B ) TYPE: amino acid
                ( C ) STRANDEDNESS: unknown
                ( D ) TOPOLOGY: unknown ( i i ) MOLECULE TYPE: protein ( x i ) SEQUENCE DESCRIPTION: SEQ ID NO:8:

Asn  Asn  Ala  Tyr  Glu  Gly  Arg
        1                    5

( 2 ) INFORMATION FOR SEQ ID NO:9:

( i ) SEQUENCE CHARACTERISTICS:
                ( A ) LENGTH: 20 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:9:

CKNCCYTCRT ANGCRTTRTT								20

( 2 ) INFORMATION FOR SEQ ID NO:10:

( i ) SEQUENCE CHARACTERISTICS:
                ( A ) LENGTH: 32 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:10:

TCGCGAATTC AATGTCAATT CCATCAAGCC AG						32

( 2 ) INFORMATION FOR SEQ ID NO:11:

( i ) SEQUENCE CHARACTERISTICS:
                ( A ) LENGTH: 30 base pairs
                ( B ) TYPE: nucleic acid
                ( C ) STRANDEDNESS: unknown
                ( D ) TOPOLOGY: unknown ( i i ) MOLECULE TYPE: DNA (genomic)

( x i ) SEQUENCE DESCRIPTION: SEQ ID NO:11:

AGATCTTACT ATGGATTAAA AACAACTCTA 30

METHOD FOR PRODUCING KETONE OR ALDEHYDE USING AN ALCOHOL DEHYDROGENASE OF *CANDIDA PARAPSILOSIS*

This is a Division of application Ser. No. 08/311,328 filed on Sep. 23, 1994 (Pending).

BACKGROUND OF THE INVENTION

1. Field of the Invention

The present invention relates to a method of producing a novel secondary alcohol dehydrogenase useful for the preparation of alcohol, aldehyde and ketone, especially for that of an optically active alcohol, a method of producing said enzyme, a DNA segment encoding said enzyme, a microorganism transformed with said DNA, and a method of producing alcohol, aldehyde and ketone, especially optically active alcohol using said enzyme.

2. Related Arts

Of the secondary alcohol dehydrogenase of the microbial origin requiring nicotinamide adenine dinucleotide phosphate (abbreviated as $NADP^+$ hereinafter), the one derived from *Thermoanaerobium brockii* is well documented (J. Am. Chem. Soc. 108, 162–169 (1986)). In addition, of the secondary alcohol dehydrogenase requiring nicotinamide adenine dinucleotide (abbreviated as $NAD^+$ hereinafter), there have been reported those derived from *Pichia sp.* NRRL-Y-11328 (Eur. J. Biochem. 101, 401–406 (1979)), *Pseudomonas sp.* SPD6 (Bioorg. Chem. 19, 398–417 (1991) ), *Pseudomonas fluorescence* NRRL B-1244 (Tokkai Sho, 59-17982), *Pseudomonas maltophilia* MB11L (FEMS Microbiol. Lett. 93, 49–56 (1992)), *Pseudomonas sp.* PED (J. Org. Chem. 57, 1526–1532 (1992)), *Pseudomonas sp.* ATCC 21439 (Eur. J. Biochem. 119, 359–364 (1981)), *Candida boidinii* SAHM (Biochim. Biophys. Acta 716, 298–307 (1992)), *Mycobacterium vaccae* JOB-5 (J. Gen. Microbiol. 131, 2901–2907 (1985)), *Rhodococcus rhodochrous* PNK1 (Arch. Microbiol. 153, 163–168 (1990)), *Comamonas terrigena* (Biochim. Biophys. Acta 661, 74–86 (1981)), and *Arthrobacter sp.* SBA (Tokkai Sho 51-57882).

However, the stereochemical substrate specificity of these secondary alcohol dehydrogenases is not satisfactory for the practical application. For example, as to 2-butanol, one of the most frequently reported substrates of the secondary alcohol dehydrogenase, there has not been reported the enzyme which will oxidize (S)-2-butanol stereospecifically to produce 2-butanone. (The enzymes derived from *Pseudomonas sp.* ATCC 21439, *Pseudomonas sp.* SPD6, *Comamonas terrigena*, *Candida boidinii* SAHM or *Pichia sp.* NRRL-Y-11328 oxidize (R)-isomer preferentially, while the one derived from *Pseudomonas fluorescens* NRRL B-1244 does not show any definite substrate stereochemical specificity, and the specificity of the enzyme derived from *Mycobacterium vaccae* JOB-5, *Rhodococcus rhodochrous* PNKb 1, *Pseudomonas sp.* PED or *Pseudomonas maltophilia* MB11L has not been reported.) Furthermore, although the primary alcohol dehydrogenase (SADH-1) derived from baker's yeast: (*Saccharomyces cerevisiae*) has been reported to oxidize 2-butanol with S configuration preferentially, the relative activity is as low as about 1% of that for ethanol, not suitable for practical use (Arch. Biochem. Biophys. 126, 933–944 (1968), J. Biol. Chem. 268, 7792–7798 (1993)).

Since the secondary alcohol dehydrogenase which will preferentially oxidize S-2-butanol has not been reported, there has been a strong demand for finding the enzyme with a high substrate stereochemical specificity.

There has been also a high demand for cloning DNA encoding said enzyme, because it will be possible to produce said enzyme on a large scale with a genetic engineering technique using the cloned gene of said enzyme.

SUMMARY OF THE INVENTION

During the wide-screening of microorganisms having the activity to preferentially oxidize (S)-2-butanol, the inventors of the present invention discovered that the microorganism belonging to genus Candida, especially Candida parapsilosis had the activity to preferentially oxidize (S)-2-butanol, further purified the enzyme to oxidize (S)-2-butanol from cells; of cultured said microorganism, and studied its enzymatic properties finding that said enzyme has the ability to oxidize (S)-2-butanol with a high stereochemical specificity and also oxidize various other secondary alcohols stereospecifically.

It is one object of the present invention to provide an enzyme with the following physicochemical properties as defined in 1) to 9):

1) Functions

Said enzyme oxidizes alcohol with $NAD^+$ as the coenzyme to produce the corresponding ketone or aldehyde, and also reduces ketone or aldehyde with NADH as the coenzyme to produce the corresponding alcohol.

2) Substrate specificity

Said enzyme utilizes aliphatic alcohols including those with an aromatic substitution as its oxidizing substrate, has a relatively higher activity toward secondary alcohols than primary ones, and preferentially oxidizes 2-butanol with the S configuration. Said enzyme also utilizes aldehydes or aliphatic ketones with an aromatic substitution.

3) Molecular weight

The apparent molecular weight of said enzyme is estimated to be approximately 40,000 by SDS-PAGE. Physicochemical as well as enzymatic properties of said enzyme of the present invention are as follows:

4) Optimal pH and pH range for the enzyme stability

The optimal pH for the oxidation of (S)-2-butanol ranges from 8.5 to 9.5, and that for the reduction of 2-butanone from 5.5 to 6.5. Said enzyme is relatively stable in the pH range from 8.0 TO 10.0.

5) Optimal temperature range for the enzymatic reaction

Said enzyme shows the high activity at the temperature ranging from 25°–55° C. with 50° C. as optimal for the enzymatic reaction.

6) Thermal inactivation

Said enzyme retains more than 90% of the original activity even after the heat treatment at 40° C. for 10 min.

7) Inhibition and stabilization

The activity of said enzyme is inhibited by various SH-reagents such as p-mercuribenzoic acid, mercuric chloride, zinc chloride and N-ethylmaleimide, and also by the reducing agents including 2-mercaptoethanol and dithiothreitol. Said enzyme activity is inhibited by o-phenanthroline but not by ethylenediaminetetraacetic acid.

8) Purification

Said enzyme can be purified to a single protein band on the sodium dodecyl sulfate polyacrylamide gel electrophoresis (abbreviated as SDS-PAGE hereinafter) by combining the conventional purification methods of ordinary proteins, comprising, for example, protamine sulfate precipitation after disrupting microbial cells, ammonium sulfate fractionation of the centrifuged supernatant, followed by a combination of anion exchange chromatography, hydrophobic chromatography and gel filtration.

9) Isoelectric point

Although said enzyme shows several bands on isoelectric focusing, the isoelectric point of the major protein band is located at pH 6.7.

The activity of all secondary alcohol dehydrogenases including said enzyme described in the preferred embodiments of the present specification was assayed as follows: (S)-2-butanol (50 µmol) and the enzyme were incubated in a reaction mixture containing Tris-HC1 (50 µmol, pH 9.0) and NAD$^+$ (2.5 µmol) at 30° C., and the rate of NADH formation was followed at 340 nm. One unit of enzyme was defined as the amount of enzyme necessary to catalyze the formation of 1 µmol of NADH per min under the assay conditions.

It is another object of the present invention to provide a DNA segment encoding said secondary alcohol dehydrogenase. Inventors of the present invention digested the purified said enzyme with lysylendopeptidase, purified the digested fragments by reversed phase chromatography, and determined a portion of its amino acid sequence using a protein sequencer. PCR (polymerase chain reaction) was performed using primers synthesized based on said amino acid sequence determined above and the chromosomal DNA of *Candida parapsilosis* as the template. A portion of gene encoding said secondary alcohol dehydrogenase was amplified and its base sequence (core sequence) was determined. Then in order to elucidate the base sequence in the flanking region of said DNA sequence determined above (core sequence), the chromosomal DNA of Candida parapsilosis was digested with HaeII, a restriction enzyme without restriction site in the core sequence. The template DNA used for reversed PCR (Nucleic Acids Res. 16, 8186 (1988)) was prepared by autorecyclarization of DNA fragments obtained above using T4 DNA ligase. Based on the core sequence, serving as the initiation site of synthesis of DNA extending from the core sequence were prepared, and the flanking region of the core sequence was amplified by the reversed PCR. By elucidating DNA sequence thus obtained it was confirmed that the entire coding region of said secondary alcohol dehydrogenase was included in the autorecircularized DNA as shown in FIGS. 6, 7 and 8 (SEQ ID No: 1 and 2). Furthermore, the product of cloned gene expressed in host *Escherichia coli* cells was confirmed to have the enzymatic activity similar to that of said secondary alcohol dehydrogenase derived from *Candida parapsilosis*.

DNA encoding said secondary alcohol dehydrogenase of the present invention includes the base sequence encoding the protein consisting of amino acid sequence essentially similar to that as shown in FIGS. 6, 7 and 8. (SEQ ID No: 2). "Essentially" in this case means that amino acid sequence shown in FIGS. 6, 7 and 8 (SEQ ID No: 2) can be modified by deletion, insertion or substitution of certain amino acid, so far as resulting proteins retain the secondary alcohol dehydrogenase activity. Needless to say DNA of the present invention includes DNA consisting of 1008 bases as shown in FIGS. 6, 7 and 8 (SEQ ID No: 1) but is not restricted to this. DNA modification which will lead to deletion, insertion or substitution in the amino acid sequence coded by DNA is suitably accomplished by conventional method such as the site-specific mutation using synthetic oligonucleotide. Further, DNA with random mutation can be obtained by performing PCR using DNA consisting of 1008 bases shown in FIGS. 6, 7 and 8 or suitably modified said DNA as the template in the presence of Mn$^{2+}$ (usually 0.5–10 mM) or lowered concentration of certain nucleotide. Needless to say, of DNAs thus obtained the present invention includes DNA encoding the protein with said secondary alcohol dehydrogenase activity.

It is another object of the present invention to provide a microorganism which is stably transformed with the DNA molecule encoding the protein having an amino acid sequence essentially similar to that shown in FIGS. 6, 7 and 8 (SEQ ID No: 2) and capable of producing said secondary alcohol dehydrogenase.

Any microorganism which can be transformed with the DNA segment encoding a peptide having said secondary alcohol dehydrogenase genase activity and is capable of expressing said activity will be the object of transformation in the present invention. Actually it comprises bacteria, yeasts and molds the host/vector system of which are well developed. Bacteria includes Escherichia, Bacillus, Pseudomonas, Serratia, Brevibacteriunm, Corynebacterium, Streptococcus and Lactobacillus. Yeasts include Saccharomyces, Kluyveromyces, Schizosaccharomyces Zygosaccharomyces, Yarrowia, Trichosporon, Rhodosporidium, Hansenula, Pichia and Candida. Molds include Neurospora, Aspergillus, Cephalosporium and Trichoderma.

A procedure or method for preparing a transformant can be performed according to the conventional technique used in the field of molecular biology, biotechnology and genetic engineering.

In order to express the gene of the present invention in microorganism, it is necessary to insert said gene into the plasmid vector or phage vector stably present in said microorganism. For expressing said DNA of the present invention in microorganism is also necessary to transcribe and translate the genetic information held in said gene. It can be accomplished by inserting a promoter and a terminator, the controlling unit for transcription and translation, into the upstream and downstream of 5'-end of said DNA of the present invention, respectively. For this purpose it is important to use a promoter and terminator which are known to function in the microorganism to be used as the host cell. Promoters and terminators usable with various microorganisms are described in detail in "Biseibutsugaku Kisokoza (Basic Microbiology), Vol. 8, Genetic Technology, Kyoritsu Shuppan (1990)", especially those usable with yeast in "Adv. Biochem. Eng. 43, 75–102 (1990)" or "Yeast 8, 423–488 (1992)".

For example, possible plasmid vectors for use with Escherichia, especially *Escherichia coli*, include the plasmid mid of pBR and pUC series, and possible promoters for use include lac promoter (β-galactosidase), trp operon (tryptophan operon), and tac promoter (lac-trp hybrid promoter), and ξ phage PL or PR-derived promoters. Furthermore, possibly terminators for use include trpA- or phage-derived rrnB ribosomal terminator.

Possible plasmid vectors for use with Bacillus include the plasmid of pUB110 series or pC194 series which can be directly inserted into chromosome. Furthermore, possible promoters or terminators for use with this species include apr (alkaline protease), npr (neutral protease) and amy (α-amylase) promoters.

Possible plasmid vectors for use with Pseudomonas, especially with *Pseudomonas putida* and *Pseudomonas cepacia* include the newly developed host vector system such as pKT240, a vector with a wide host cell spectrum derived from TOL plasmid participating in the toluene decomposition (vector also includes the gene necessary for the autonomous replication derived from RSF1010 and others), and possible promoters and terminators include the lipase gene (JPH5-284973).

Possible plasmid vectors for use with Brevibacterium, especially with *Brevibacterium lactofermentum* include pAJ43, and possible promoters and terminators for use are the same as those used with Escherichia.

Possible plasmid vectors for use with Corynebacterium, especially with *Corynebacterium glutamicum* include pCS11 (JPS57-183799) and pCB101 (Mol. Gen. Genet. 196, 175 (1984)).

Possible plasmid vectors for use with Streptococcus include those such as pHV1301 (FEMS Microbiol. Lett. 26, 239 (1985)) and pGK1 (Appl. Environ. Microbiol. 50, 94 (1985)).

Possible plasmid vectors for use with Lactobacillus are those developed for use with Streptococcus such as pAMβ1 (J. Bacteriol. 137, 614 (1979)), and possible promoters for use are those for use with Escherichia.

Possible plasmid vectors for use with Saccharomyces, especially *Saccharomyces cerevisiae* include those of series YRp, YEp, YCp and YIp. Integration vector (e.g., in EP 537456) constituted by utilizing homologous recombination with ribosomal DNA having multicopy in the chromosome is useful for the insertion of multicopy and for the stable gene retention. In addition, plasmid vectors carrying ADH (alcohol dehydrogenase), GAPDH (glyceraldehyde 3-phosphate dehydrogenase), PHO (acid phosphatase), GAL (β-galactosidase), PGK (phosphoglycerate kinase) and ENO (enolase) are also usable as the promoter or terminator with this species.

Possible plasmid vectors for use with Kluyveromyces, especially *Kluyveromyces lactis* include 2 µm series plasmid derived from *Saccharomyces cerevisiae*, pKD1 series plasmid (J. Bacteriol. 145, 382–390 (1981)), pGK11-derived plasmid related to killer activity, KARS series plasmid with the autonomous replication gene of Kluyveromyces and integration vector (e.g., in EP 537456) which can integrate in the gene by homologous replication with ribosomal DNA. Vectors inserted the gene encoding ADH or PGK are also usable as the promoter or terminator.

Possible plasmid vectors for use in Schizosaccharomyces include those with the insertion of a) ARS (gene related to autonomous replication) derived from *Schizosaccharomyces pombe*, b) the selective marker derived from *Saccharomyces cerevisiae* and complementary to auxotrophy (Mol. Cell Biol. 6, 80 (1986)), and c) ADH promoter derived from *Saccharomyces pombe* (EMBCO J. 6, 729 (1987)).

Possible plasmid vectors for use in Zygosaccharomyces include pSB3 derived from *Zygosaccharomyces rouxii* (Nuclei Acids Res. 13, 4267 (1985)), PHO5 promoter derived from *Saccharomyces cerevisiae*, and GAP-Zr (carrying the gene for glyceraldehyde 3-phosphate dehydrogenase) promoter derived from *Zygosaccharomyces rouxii* (Agri. Biol. Chem. 54, 2521 (1990)).

Possible plasmid vectors for use in Hansenula include the host vector system developed in *Hasenula polymorpha* comprising HARS1 and HARS2, the autonomous replication sequence from *Hansenula polymorpha*, which, however, are relatively unstable. Therefore, the integration vector carrying multicopy in chromosome is useful (Yeast 7, 431–448 (1991)). Promoters for methanol-inducible AOX (alcohol dehydrogenase) or FDH (formate dehydrogenase) are also useful.

Possible plasmid vectors for use in Pichia include the host vector system developed in *Pichia pastoris* using the gene participating in the autonomous replication in Pichia (Mol. Cell. Biol. 5, 3376 (1985)) and the potent promoter for AOX inducible by the high concentration culture in the presence of methanol (Nucleic Acid Res. 15, 3859 (1987)).

As possible plasmid vectors for use in Candida the host vector system has been developed in *Candida maltosa*, *Candida albicans* and *Candida tropicalis*. In *Candida maltosa*, the plasmid vector with the insertion of cloned ARS (autonomous replication sequence) derived from *Candida maltosa* (Agri. Biol. Chem. 51, 51, 1587 (1987)) has been developed for use.

Possible plasmid vectors for use in Aspergillus, one of the most thoroughly studied molds, include the vector constructed by the integration of gene into the plasmid or chromosome and the promoter for the extracellular protease or amylase (Trends in Biotechnology 7, 283–287 (1989)).

As possible plasmid vectors for use in Trichoderma, the host vector system has been developed in *Trichoderma reesei*, and the promoter for the extracellular cellulase is useful for the vector construction (Biotechnology 7, 596–603 (1989)).

A method of producing the enzyme of the present invention comprises culturing cells belonging to genus Candida or its mutant having the producibility of said enzyme with the following properties 1) to 3) or recombinant cells endowed with the producibility of said enzyme by inserting the gene encoding said enzyme into a foreign microorganism host.

1) Function

Said enzyme oxidizes alcohol with $NAD^+$ as the coenzyme producing corresponding ketone or aldehyde. Also said enzyme reduces ketone or aldehyde with NADH as the coenzyme producing corresponding alcohol.

2) Substrate specificity

Said enzyme utilizes aliphatic alcohols with aromatic substitution as the substrate for its oxidation reaction, showing higher activity toward secondary alcohols as compared with primary ones and oxidizing (S)-2-butanol preferentially. Aldehydes or ketones with aromatic substitution are the substrate for reduction reaction of said enzyme.

3) Molecular weight

The apparent molecular weight of said enzyme is estimated to be about 40,000 by SDS-PAGE.

Furthermore, said enzyme of the present invention, or microorganism containing said enzyme (including its mutant strain and recombinant microorganism), or the processed product thereof can be used to react with the racemic aliphatic alcohol with a possible aromatic substitution such as 2-butanol, 2-octanol, phenoxyethanol, 1,3-butanediol and ethyl β-hydroxy-n-butylate, oxidizing only one of the optically active isomers (e.g., (S)-isomer in the case of 2-butanol, 2-octanol, phenylethanol, 1,3-butanediol and ethyl β-hydroxy-n-butylate) and producing the other optically active isomer (R-isomer in the case of 2-butanol, 2-octanol, phenylethanol, 1,3-butanediol and ethyl β-hydroxy-n-butylate). In this oxidation reaction the coenzyme $NAD^+$ is reduced to NADH.

NADH thus produced can be converted (regenerated) to $NAD^+$ by, for example, the microbial ability to convert NADH to $NAD^+$. $NAD^+$ can be regenerated by adding the enzyme having the activity to oxidize NADH to $NAD^+$ such as glutamate dehydrogenase, glucose dehydrogenase, NADH dehydrogenase and NADH oxidase, or microorganisms containing these enzymes or the processed products thereof to the reaction system. Taking advantage of the substrate specificity of said enzyme of the present invention, a simultaneous regeneration of $NAD^+$ with said enzyme alone can be accomplished by adding inexpensive substrate of reducing reaction of said enzyme such as acetone or 2-butanone to the reaction system.

Also an optically active alcohol can be produced by treating the corresponding ketonic compound with said secondary alcohol dehydrogenase of the present invention or microorganism producing said enzyme (including its mutant strain or recombinant cell) or the processed product thereof; for example, (S)-2-butanol from 2-butanone, (S)-octanol from 2-octanone, (S)-1-phenylethanol from acetophenone, (S)-1,3-butanediol from 4-hydroxy-2-butanone, (S)-β-hydroxy-n-butylic acid ester from acetoacetic acid ester. By this reducing reaction, the coenzyme NADH is oxidized to generate $NAD^+$.

$NAD^+$ thus produced can be converted (regenerated) to NADH by, for example, the activity of microorganism to convert $NAD^+$ to NADH. The $NAD^+$ reducing activity can be amplified by adding glucose, ethanol or formate to the reaction system. $NAD^+$ can be reduced also by adding the enzyme capable of reducing $NAD^+$ to NADH such as formate dehydrogenase, malate dehydrogenase and glucose dehydrogenase, or by adding microorganism containing these enzymes or the processed product thereof to the reaction system. Taking advantage of the substrate specificity of said enzyme, simultaneous regeneration of NADH can be accomplished with said enzyme alone by adding the substrate of oxidative reaction of said enzyme such as isopropanol or ethanol to the reaction system.

BRIEF DESCRIPTION OF THE DRAWING

FIG. 6 shows the base sequence of DNA encoding said secondary alcohol dehydrogenase.(SEQ ID No: 1) amino acid sequence (SEQ ID No: 2) deduced from said base sequence and the regions of PCR and reversed PCR primers in said sequence.

FIG. 7 shows the base sequence of DNA encoding said secondary alcohol dehydrogenase, amino acid sequence deduced from said base sequence and the regions of PCR and reversed PCR primers in said sequence (continuation of FIG. 6).

FIG. 8 shows the base sequence of DNA encoding said secondary alcohol dehydrogenase, amino acid sequence deduced from said base sequence and the regions of PCR and reversed PCR primers in said sequence (continuation of FIG. 7).

FIG. 9 shows the base and amino acid sequences of the mixed PCR primers (CpN and CpT10). SEQ ID Nos: 3,4,7,8 and 9. Plural bases assigned to the same position in the Figure indicate that the primer is a mixture of primers with plural codons for amino acid.

PREFERRED EMBODIMENTS

In the following section, preferred embodiments describe the present invention in greater detail. However, the present invention is not restricted to the example presented here.

EXAMPLE 1

Purification of Secondary Alcohol Dehydrogenase

Candida piarapsilosis IFO 1396 strain was grown in a YM medium containing glucose (10 g), bactopepton (5 g), yeast extract (3 g) and malt extract (3 g) per liter at pH 6.0. Cells were harvested by centrifugation.

The wet cells thus obtained were disrupted in a high pressure cell disintegrator, and centrifuged to remove cell debris. To the cell-free extract protamine sulfate was added to remove nucleic acids and microsomes. After centrifugation, the supernatant was brought to 70% saturation with ammonium sulfate, and the precipitate was collected, subjected to anion exchange chromatography on Q-Sepharose FF, eluted with a density gradient of NaCl, and the peak fraction containing said secondary alcohol dehydrogenase activity was collected. The active fraction was then subjected to hydrophobic chromatography on a column of phenyl-Sepharose equilibrated with a buffer containing 1.62M ammonium sulfate, and the active fraction was eluted by reducing the ammonium sulfate concentration to 0M (the enzyme activity was assayed as described hereinbefore). After the active fraction was added to a Red Sepharose affinity column, the unretained fraction was subjected to a Superdex 200 gel filtration. The recovered active fraction was subjected to anion exchange chromatography on a Mono Q column and eluted with a density gradient of NaCl. Only active fractions which gave a single band in the purity test on SDS-PAGE were collected.

On polyacrylamide gel electrophoresis (Native-PAGE), the purified secondary alcohol dehydrogenase gave one major and several adjacent minor weak protein bands. On activity staining, all protein bands showed the secondary alcohol dehydrogenase activity, and on SDS-PAGE this enzyme preparation migrated as a single protein band.

Figure 1:
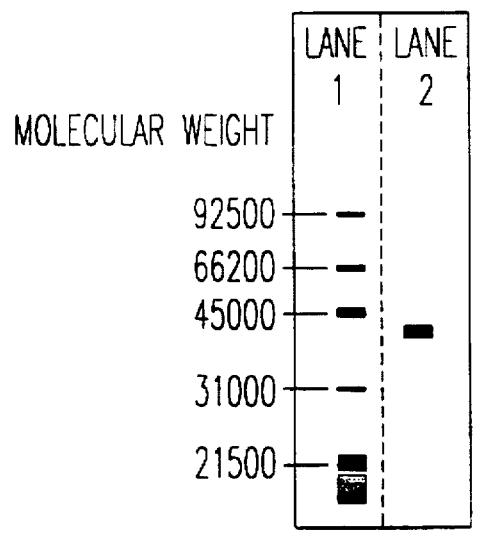
FIG. 1 shows the electrophoretic pattern of the purified said secondary alcohol dehydrogenase on sodium dodecyl-sulfate polyacrylamide gel.

The apparent molecular weight of the purified enzyme estimated by SDS-PAGE was about 40,000 (FIG. 1).

Table 1 summarizes the procedure that resulted in a purification cation of the enzyme with a specific activity of 1370 units/mg.

TABLE 1

| | Volume (ml) | Total amount of protein (mg) | Total activity (U) | Specific activity (U/mg) | Yield (%) |
|---|---|---|---|---|---|
| Crude extract | 4,800 | 157,000 | 40,100 | 0.255 | 100.0 |
| Protamine sulfate | 5,200 | 94,600 | 35,200 | 0.371 | 87.6 |
| $(NH_4)_2SO_4$ (0–70%) | 550 | 78,700 | 30,700 | 0.390 | 76.5 |
| Q-Sepharose FF | 550 | 8,870 | 9,730 | 1.10 | 24.2 |
| Phenyl Sepharose | 22 | 191 | 5,440 | 28.5 | 13.6 |
| Red-Sepharose | 2.4 | 22.1 | 6,150 | 279 | 15.3 |
| Superdex 200 | 5.34 | 3.7 | 3,140 | 846 | 7.8 |
| Mono-Q | 1.05 | 1.7 | 2,360 | 1,370 | 5.9 |

EXAMPLE 2 pH Optimum of Secondary Alcohol Dehydrogenase

Figure 2:
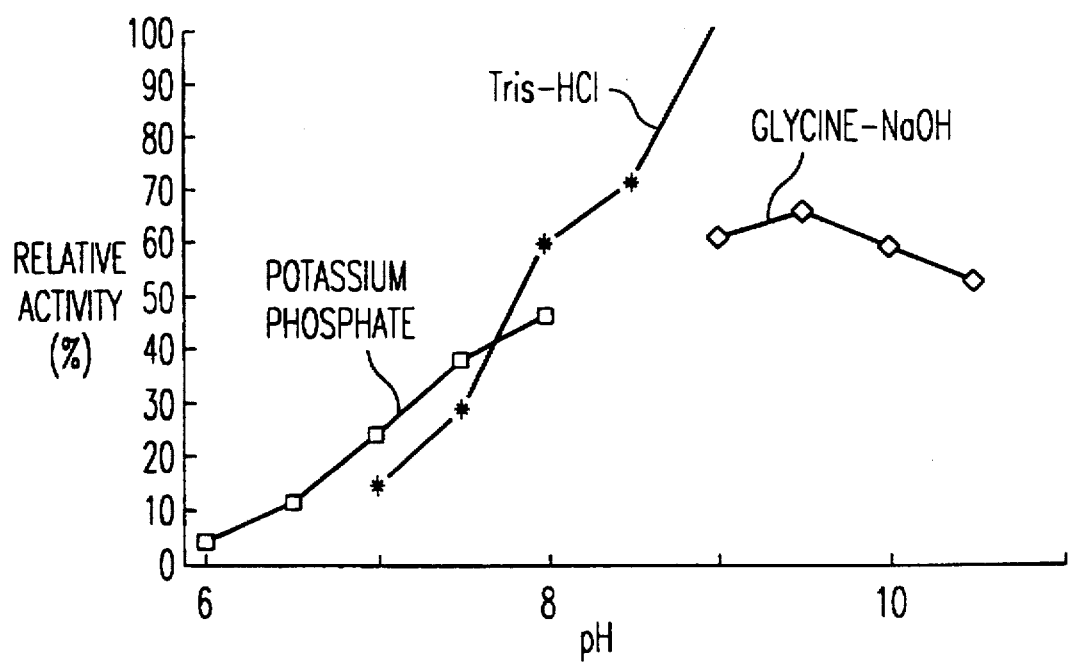
FIG. 2 shows the effect of pHs on the (S)-2-butanol oxidizing activity of said secondary alcohol dehydrogenase, expressed as relative to the maximum activity (100%) at the optimum pH.
Figure 3:
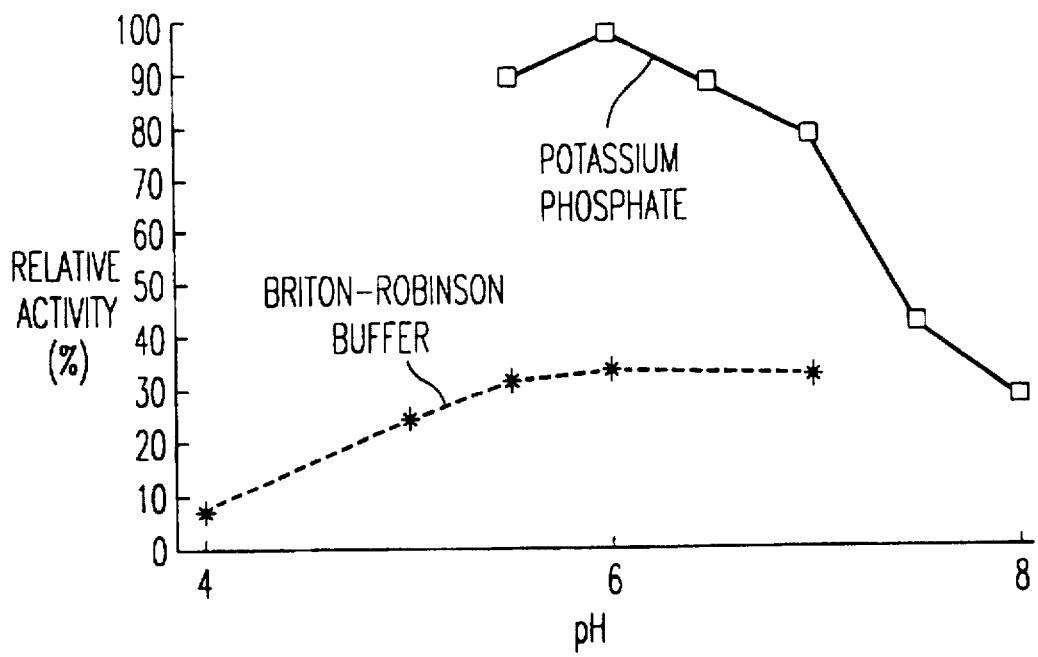
FIG. 3 shows the effect of pHs on the 2-butanone reducing activity of said secondary alcohol dehydrogenase, expressed as relative to the maximum activity (100%) at the optimum pH.

The effect of pH on the (S)-2-butanol oxidizing activity and 2-butanone reducing activity (assayed under the conditions for (S)-2-butanol oxidizing activity assay in the presence of NADH (0.4 μmol in stead of NAD+, following the rate of the oxidation of NADH at 340 nm) was examined under different pHs using potassium phosphate (KPB), Tris-HCl and Briton-Robinson buffer. The enzyme activity relative to the maximum activity (100%) was shown in FIGS. 2 and 3. The pH optimum for the oxidation of (S)-2-butanol was 8.5–9.5, while that for the reduction of 2-butanone was 5.5–6.5.

EXAMPLE 3

Optimum Reaction Temperature for Secondary Alcohol Dehydrogenase

The secondary alcohol dehydrogenase activity was assayed under the standard assay conditions at different temperature as shown in Table 2. The optimum reaction temperature of said enzyme was found to be 50° C.

TABLE 2

| Temperature (°C.) | 30 | 37 | 45 | 50 | 55 | 60 |
|---|---|---|---|---|---|---|
| Relative activity (%) | 55 | 65 | 92 | 100 | 88 | 0 |

EXAMPLE 4 pH Stability of Secondary Alcohol Dehydrogenase

Figure 4:
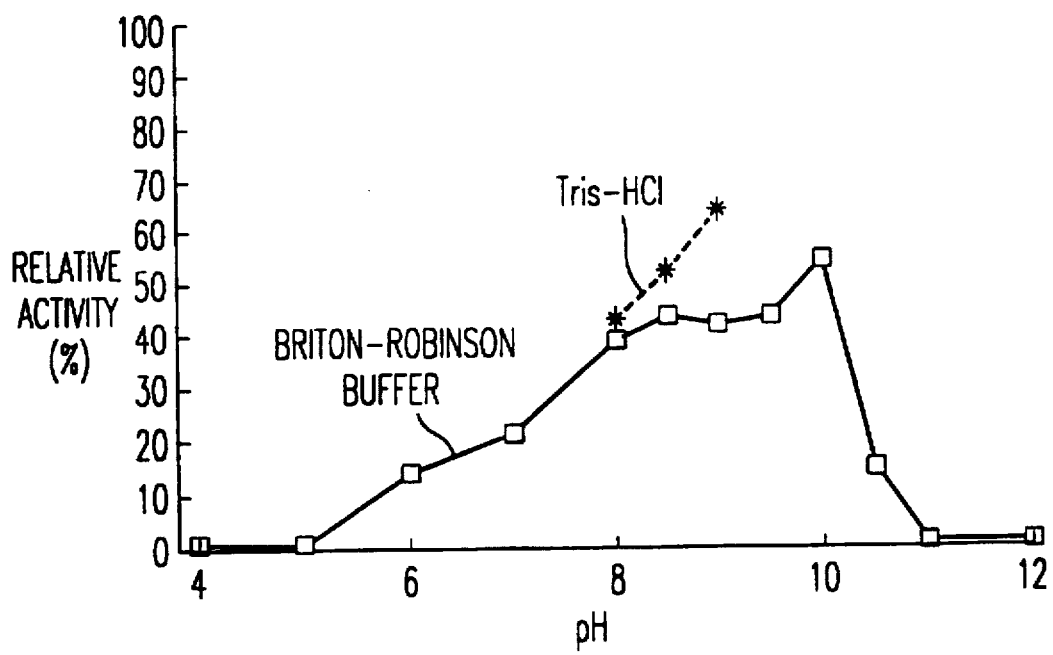
FIG. 4 shows the effect of pHs on the remaining activity of said secondary alcohol dehydrogenase after the treatment of said enzyme at 30° C. for 30 min, expressed as relative to the initial activity (100%).

After the purified enzyme was incubated in Tris-HCl (pH 8.02–9.0) and Briton-Robinson buffer (pH 5.0–12.0) at 30° C. for 30 min, the remaining activity was assayed. Said enzyme was most stable at pH ranging from 8 to 10.0 (FIG. 4).

EXAMPLE 5

Thermostibility of Secondary Alcohol Dehydrogenase

Figure 5:
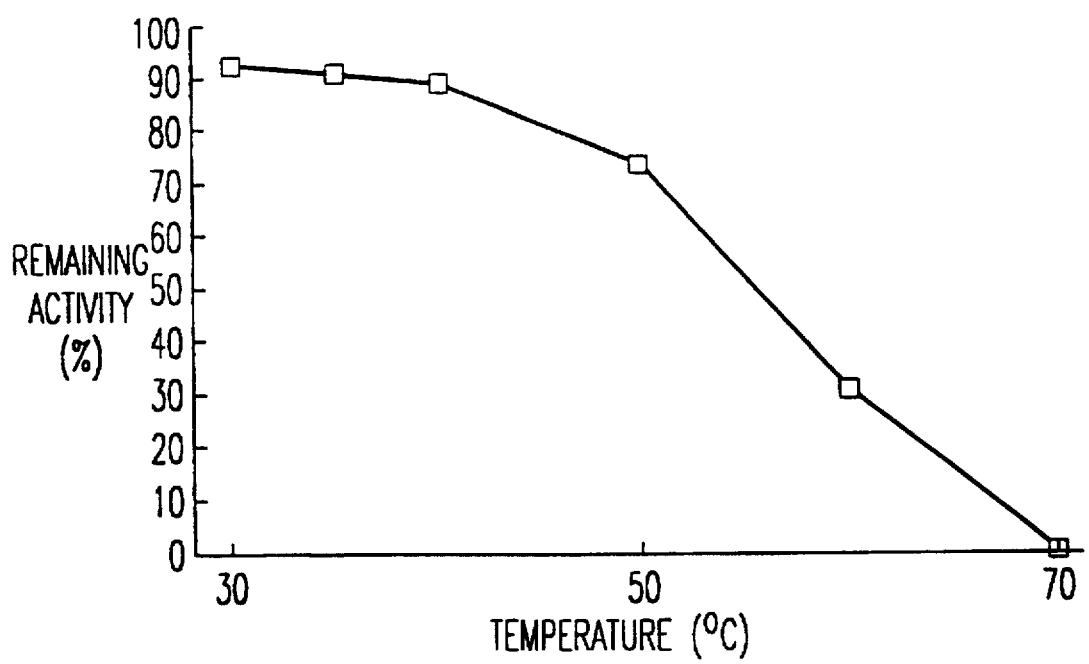
FIG. 5 shows the effect of heating at different temperature for 10 min on the remaining activity of said secondary alcohol dehydrogenase, expressed as relative to the initial activity (100%).

After the purified enzyme was incubated at pH 8.0 and 30° C.–70° C. for 10 min, the remaining activity was assayed. Even after the incubation at 40° C. for 10 min, more than 90% of the original enzyme activity was retained (FIG. 5).

EXAMPLE 6

Substrate Specificity of Secondary Alcohol Dehydrogenase

The oxidizing and reducing activities of said enzyme with various alcohols and aldehydes as the substrate respectively are summarized in tables 3 and 4 respectively as compared with the (S)-2-butanol oxidizing activity (100%) and 2-butanone reducing activity (100%) respectively.

TABLE 3

| Oxidation Substrate | Concentration (mM) | Coenzyme | Relative activity (%) |
|---|---|---|---|
| 2-Propanol | 100 | NAD+ | 60.0 |
| (S)-2-Butanol | 50 | NAD+ | 100.0 |
| (R)-2-Butanol | 50 | NAD+ | 3.3 |
| (RS)-2-Butanol | 100 | NAD+ | 43.5 |
| 2-Pentanol | 100 | NAD+ | 34.0 |
| 3-Pentanol | 100 | NAD+ | 10.4 |
| 2-Hexanol | 50 | NAD+ | 27.7 |

TABLE 3-continued

| Oxidation Substrate | Concentration (mM) | Coenzyme | Relative activity (%) |
|---|---|---|---|
| (S)-2-Octanol | 5 | NAD+ | 67.7 |
| (R)-2-Octanol | 5 | NAD+ | 0.0 |
| (RS)-2-Octanol | 5 | NAD+ | 39.2 |
| Cyclohexanol | 20 | NAD+ | 52.8 |
| (S)-1-Phenylethanol | 50 | NAD+ | 89.3 |
| (R)-1-Phenylethanol | 50 | NAD+ | 1.1 |
| (S)-1,3-Butanediol | 50 | NAD+ | 17.8 |
| (R)-1,3-Butanediol | 50 | NAD+ | 0.3 |
| 2,4-Pentanediol | 100 | NAD+ | 42.6 |
| (2R,4R)-2,4-Pentanediol | 50 | NAD+ | 0.1 |
| 4-Methyl-2-pentanol | 20 | NAD+ | 40.8 |
| (S)-1-Amino-2-propanol | 50 | NAD+ | 3.2 |
| (R)-1-Amino-2-propanol | 50 | NAD+ | 7.9 |

TABLE 4

| | Oxidation Substrate | Concentration (mM) | Coenzyme | Relative activity (%) |
|---|---|---|---|---|
| | (RS)-2-Hydroxy-butyric acid | 100 | NAD+ | 0.3 |
| | Methanol | 100 | NAD+ | 0.2 |
| | Ethanol | 100 | NAD+ | 1.0 |
| | Aryl alcohol | 100 | NAD+ | 2.4 |
| | 1-Propanol | 100 | NAD+ | 1.5 |
| | 1-Butanol | 100 | NAD+ | 2.3 |
| | 1-Pentanol | 100 | NAD+ | 1.2 |
| | (S)-1,2-Propanediol | 50 | NAD+ | 2.5 |
| | (R)-1,2-Propanediol | 50 | NAD+ | 2.0 |
| Reduction | 2-Butanone | 100 | NADH | 100.0 |
| | Acetone | 100 | NADH | 123.4 |
| | Acetophenone | 20 | NADH | 121.8 |
| | Propionaldehyde | 100 | NADH | 76.2 |
| | 4-Hydroxy-2-butanone | 100 | NADH | 41.2 |
| | 3-Hydroxy-3-methyl-2-butanone | 100 | NADH | 18.5 |

EXAMPLE 7

Inhibitor of Secondary Alcohol Dehydrogenase

After said enzyme was incubated at 30° C. for 30 min in the presence of various reagents, the remaining activity was assayed and expressed as the percentage relative to that (100%) of the untreated enzyme (Table 5).

TABLE 5

| Inhibitor | Concentration (mM) | Relative activity (%) |
|---|---|---|
| Phenylmethane-sulfonyl fluoride | 1 | 69.0 |
| p-Chloromercuri-benzoic acid | 0.05 | 0.0 |
| N-Ethylmaleimide | 1 | 21.2 |
| Iodoacetic acid | 1 | 52.0 |
| Ethylenediamine-tetraacetic acid | 1 | 102.5 |
| o-Phenanthroline | 1 | 19.0 |
| $HgCl_2$ | 1 | 0.0 |
| $CuSO_4$ | 1 | 25.5 |
| $ZnCl_2$ | 1 | 16.4 |
| Dithiothreitol | 1 | 0.0 |

TABLE 5-continued

| Inhibitor | Concentration (mM) | Relative activity (%) |
|---|---|---|
| b-Mercaptoethanol | 1 | 3.2 |
| $NH_2OH$ | 0.01 | 92.7 |
| $NaN_3$ | 0.02(%) | 89.9 |
| Crotonic acid | 50 | 89.6 |

The enzyme activity was markedly inhibited by dithiothreitol (DTT), iodoacetamide, p-chloromercuribenzoic acid, mercuric chloride, zinc chloride, metal chelator (at high concentration) and 2-mercaptoethanol.

EXAMPLE 8

Analysis of the Partial Amino Acid Sequence of Secondary Alcohol Dehydrogenase

The purified enzyme (0.153 mg) in 50 mM Tris-HCl (pH 9.0) containing 4M urea was digested with lysylendopeptidase (0.53 µg) at 30° C. for 6 h. Peptide fragments thus obtained were fractionated by a reversed phase HPLC (on a TSK ODS-120T column, TOSO), and eluted with a density gradient of acetonitrile in 0.1% trifluoroacetic acid. The amino acid sequence of fractionated peptides were determined by a protein sequence 477A (ABI), and shown in FIGS. 6, 7 and 8 (underlined).

EXAMPLE 9

PCR Cloning of Gene Encoding Secondary Alcohol Dehydrogenase

A DNA fragment with the sequence deduced from the amino acid sequence near the N-terminal was synthesized, in consideration of its degeneracy, as a mixed PCR primer (CpN) (SEQ ID No: 3). Another DNA sequence complementary to that deduced from the amino acid sequence near the C-terminal was synthesized as another mixed PCR primer (CpT10) (SEQ ID No: 9). These base sequences are shown in FIG. 9. DNA synthesis was carried out with an ABI DNA synthesizer 381A.

EXAMPLE 10

Preparation of Chromosomal DNA from Candida Parapsilosis

*Candida parapsilosis* IFO 1396 was grown in a YEPD medium (100 ml) (1% yeast extract, 2% polypeptone and 2% glucose) and centrifuged. (Cells were suspended in 0.1M ethylenediaminetetraacetic acid (EDTA) containing 25 mM sorbitol and centrifuged again. To the recovered cells suspended in 50 mM potassium phosphate (pH 7.5, 10 ml) containing 1M sorbitol, 0.1M 2-mercaptoethanol, chymolyase (0.4 ml) was added, and the mixture was incubated at 30° C. to obtain protoplast. After the formation of protoplast was confirmed under the microscope, the mixture was centrifuged. To the recovered cells resuspended in 50 mM Tris-HCl (pH 7.4, 12 ml) containing 20 mM EDTA, 10% SDS (sodium dodecylsulfate, 1.2 ml) was added, thoroughly mixed, and incubated at 65° C. for 80 min. Then, after the addition of 5M potassium acetate (pH 5.0, 3.6 ml), the mixture was left on ice for 60 min to precipitate the denatured protein.

After removing the denatured protein by centrifugation, an equal volume of isopropanol was added to the recovered supernatant, and gently mixed. Precipitated DNA was collected by centrifugation, dried, dissolved in 10 mM Tris-HCl (pH 7.4) containing 1 mM EDTA. To this mixture, RNase (1 mg/ml, 0.75 ml) was added, and incubated at 37° C. for 1 h to degrade contaminating RNA. Then after the successive extraction with phenol, phenol/chloroform, and phenol, DNA was recovered by ethanol precipitation and used as the template for PCR described in Example 11.

EXAMPLE 11

Cloning of Secondary Alcohol Dehydrogenase Gene by PCR

Using said chromosomal DNA of *Candida parapsilosis* (50 ng) prepared in Example 10 as the template, PCR was performed for amplification in a PCR buffer [10 mM Tris-HCl (pH 8.3), 50 mM KCl, 1.5 mM $MgCl_2$, 0.2 mM each dNTP, 0.01% gelatin, and 2 units TaqDNA polymerase (Roche)] with a set of said mixed PCR primers (CpN and CpT10, 100 pmol each) synthesized in Example 9. After 30 cycles of heat denaturation (94° C., 30 sec), annealing (45° C., 30 sec) and extension (60° C., 2 min), the PCR mixture was cooled to 4° C., and the amplification of DNA was confirmed by agarose-gel electrophoresis of the PCR products.

EXAMPLE 12

Subcloning of DNA Amplified by PCR

The DNA amplified by PCR in Example 11 was subcloned into pUC18 with a SureClone Ligation Kit (Pharmacia). The base sequence of the construct determined with an ABI DNA Sequencer 373A was found to consist of 971 bases including the sequence of said PCR primers, CpN and CpT10, (SEQ ID No: 9) which sandwiched said DNA sequence between them as shown in FIGS. 6, 7 and 8 (SEQ ID No: 1). This sequence is designated as "core sequence" hereinafter.

EXAMPLE 13

Cloning of Base Sequence Surrounding the Core Sequence by Reversed PCR

The base sequence complementary to a region near the 5'-side of the core sequence, CAATTGAC-CCGCTTTGGGC (CPA-MUN) (SEQ ID No: 5) and that to a region near the 3'-side, TTCGAATCTTGGG-TAGTTTTTG (CPA-NSP) were (SEQ ID No: 6) synthesized as the reversed PCR primers. Regions of these primers in the DNA molecule encoding said secondary alcohol dehydrogenase are shown in FIGS. 6, 7 and 8.

Chromosomal DNA of *Candida parapsilosis* was digested with a restriction enzyme HaeII and the digest was selfcircularized by T4 DNA ligase to be used as the template of reversed PCR.

PCR was performed in the PCR buffer (described in Example 11) containing auto-recircularization product (50 ng) and a set of said synthetic primers, CPN-MUN and CPA-NSP (20 pmol each). After 30 cycles of heat-denaturation (94° C., 30 sec), annealing (50° C., 30 sec) and extension reaction (70° C., 2 min), the amplified DNA fragment was subcloned into pUC18 with a SureClone Ligation Kit (Pharmacia) and then the entire base sequence was determined with an ABI DNA Sequencer as described in Example 12.

EXAMPLE 14

Synthesis of the Gene Encoding Secondary Alcohol Dehydrogenase by PCR

The restriction site was introduced to the DNA molecule encoding said enzyme by PCR with appropriate primers.

Using said DNA prepared in Example 10 as the template, PCR was performed for amplification of a DNA fragment of about 1030 bp with a 5'-primer [CPA-ATG] (5'-TCGCGAATTCAAIAATTCCATCAAGCCAG-3') (SEQ ID No: 10) having the EcoRI restriction site and a 3'-primer [CPA-TAG] (5'-AGATCTTACTATGGATTAAAAACAACTCTA-3') (SEQ ID No: 11) having the BglII restriction site. DNA was synthesized with an ABI DNA Synthesizer 381A as in Example 11.

EXAMPLE 15

Subcloning of DNA Amplified by PCR

Figure 10:
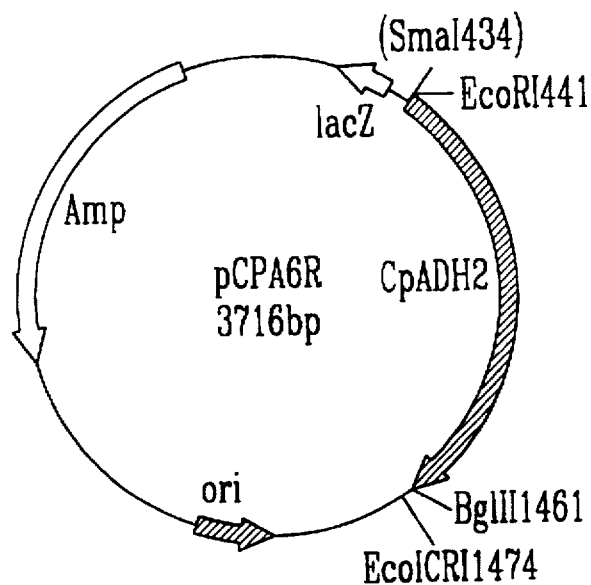
FIG. 10 shows the construction of plasmid pCPA6R.

The PCR fragment amplified as described in Example 14 was subcloned into the SmaI site of pUC18 having multi-cloning sites with SureClone Ligation Kit (Pharmacia) (FIG. 10). In the constructed plasmid (designated as pCPA6R), the lactose promoter was inserted in the opposite direction (included in the region designated as "lac Z" in FIG. 10).

EXAMPLE 16

Figure 11:
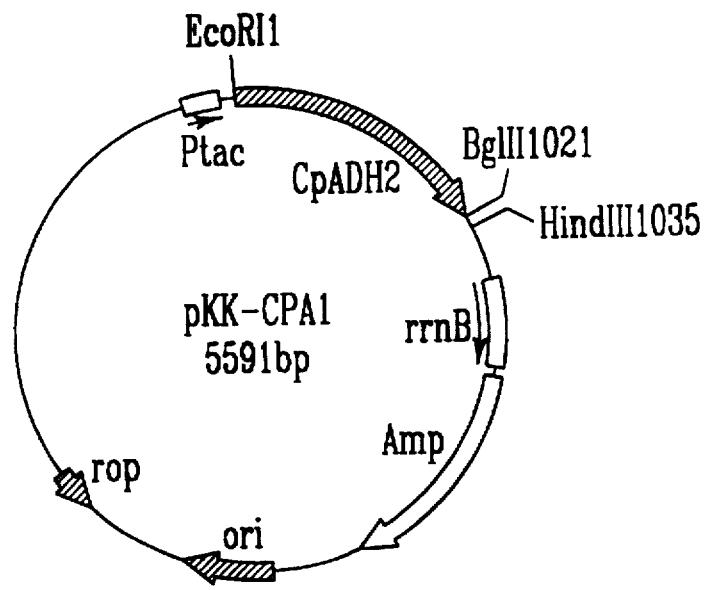
FIG. 11 shows the construction of expression vector pKK-CPA1.

Construction of Plasmid pKK-CPA1, Gene for the Expression of Secondary Alcohol Dehydrogenase Said gene of said secondary alcohol dehydrogenase was subcloned into the expression vector pKK223-3 (Pharmacia) by the following procedure and the construct was designated as pKKCPA1. Said plasmid pCPA6R was digested by EcoICRI (Promega), linked with HindIII linker (Takara) and then cleaved with EcoRI (Takara) and HindIII (Takara) to extract the DNA fragment encoding said secondary alcohol dehydrogenase. Then said DNA fragment was linked to the cleaved product of the expression vector, pKK223-3 with restriction enzymes EcoRI and HindIII to construct the gene expression vector for said secondary alcohol dehydrogenase, pKK-CPA1 (FIG. 11).

EXAMPLE 17

Production of Said Secondary Alcohol Dehydrogenase

Competent cells of Escherichia coli JM109 were prepared and transformed with said expression vector pKK-CPA1 to produce a said secondary alcohol dehydrogenase producing strain. This strain was grown in an LB medium (consisting of 1% polypeptone, 0.5% yeast extract and 1.0% NaCl, pH 7.2) containing ampicillin (0.1 mg/ml) at 30° C. for 3 h. After the addition of isopropylthiogalactoside (IPTG) to a 1 mM final concentration, the culture was incubated for further 5 h, then the culture was centrifuged to collect cells.

EXAMPLE 18

Activity Evaluation of Transformed Cells by Enzymatic Reaction

The cells prepared according to Example 17 were suspended in 50 mM Tris-HCl (pH 9.0) containing 0.01% 2-mercaptoethanol, and sonicated to obtain the crude enzyme solution. Said enzyme solution was added to a reaction mixture consisting of 50 mM Tris-HCl (pH 9.0), 50 mM (S)-1,3-butanediol and 2.5 mM $NAD^+$, and the rate of $NAD^+$ reduction was followed at 340 nm. Results of (S)-1, 3-butanediol oxidizing activity thus assayed are shown in Table 6. As the control, results of similar activity assay of the host Escherichia coli cells which were not transformed with the expression plasmid pKK-CPA1 are also shown in Table 6.

TABLE 6

| Strain | Specific activity (Unit/mg) |
|---|---|
| Escherichia coli JM109 (pKK-CPA1) | 0.581 |
| Escherichia coli JM109 | 0.0 |

EXAMPLE 19

Production of (R)-1,3-Butanediol by Recombinant Bacteria Cells

To the cells prepared according to Example 17, racemic 1,3-butanediol butanediol and $CaCO_3$ were added to a final concentration of 5% and 0.8% respectively, and the mixture was incubated in test tubes of 21-mm diameter at 30° C. for 17 h on shaking (250 rpm). Cell concentration at the beginning of reaction was adjusted to $A_{650}=20$. After the reaction, cells were removed by centrifugation, and the supernatant (500 μl) was saturated with NaCl, and then the remaining 1,3-butanediol was extracted with ethyl acetate (2 ml). After the removal of solvent from the extract, the residue was acetylated by the addition of acetyl chloride (100 μl). Aceylated 1,3-butanediol was dissolved in n-hexane (1 ml), and the optical purity was assayed by high performance liquid chromatography on an optical resolution column [Chiralcel OB (Daicel Chem. Ind.); solvent, n-hexane/2-propanol=19/1; wave length, 220 nm; elusion rate, 1.0 ml/min; temperature, 40° C. ] (retention time: (S)-isomer, 15 min; (R)-isomer, 19.3 min).

Furthermore, after the supernatant described above was appropriately diluted with distilled water, the concentration of 1,3-butanediol therein was determined by gas chromatography [column (3 mm in diameter×2.1 m in length), Thermon 3000 5%/chromosorb W 80–100 mesh (Shinwakako); temperature, 130° C.]. The optical purity and yield of 1,3-butanediol were summarized in Table 7. As the control, results of similar assay with the host Escherichta coli cells which were not transformed with the expression plasmid pKK-CPA1 were also listed in Table 7. Yield in Table 7 is "the molar ratio of the remaining 1,3-butanediol after the reaction to the initial racemic 1,3-butanediol added".

TABLE 7

| Strain | Optical purity (% ee R) | Yield (%) |
|---|---|---|
| Escherichia coli JM109 (pKK-CPA1) | 93.2 | 48.3 |
| Escherichia coli JM109 | 0.0 | 88.8 |

By the present invention it became possible to obtain a novel secondary alcohol dehydrogenae with stereochemical specificity, DNA encoding said enzyme, and microorganism transformed by DNA encoding said enzyme.

Using said enzyme, the microorganism (including its mutant and transformant) producing said enzyme, or the processed products thereof, it became possible to produce an optically active alcohol from the racemic alcohol or asymmetric ketone.

We claim:

1. A method of producing alcohol comprising reacting ketone or aldehyde with an alcohol dehydrogenase isolated from *Candida parapsilosis* having the following characteristics:
   (a) said alcohol dehydrogenase oxidizes an alcohol using $NAD^+$ as a coenzyme to produce a ketone or aldehyde;
   (b) said alcohol dehydrogenase reduces a ketone or aldehyde using NADH as a coenzyme to produce an alcohol;
   (c) said alcohol dehydrogenase has higher activity on secondary alcohols than primary alcohols; and
   (d) said alcohol dehydrogenase preferentially oxidizes 2-butanol having an S-configuration; or with a microorganism producing said enzyme or a crude enzyme solution prepared by disrupting said microorganism and reducing said ketone or aldehyde to alcohol.

2. The method of claim 1, wherein the enzyme is derived from a microorganism transformed with a DNA encoding the amino acid sequence of SEQ ID NO:2.

3. A method of producing an optically active alcohol comprising reacting asymmetric ketone with an alcohol dehydrogenase isolated from *Candida parapsilosis* having the following characteristics:
   (a) said alcohol dehydrogenase oxidizes an alcohol using $NAD^+$ as a coenzyme to produce a ketone or aldehyde;
   (b) said alcohol dehydrogenase reduces a ketone or aldehyde using NADH as a coenzyme to produce an alcohol;
   (c) said alcohol dehydrogenase has higher activity on secondary alcohols than primary alcohols; and
   (d) said alcohol dehydrogenase preferentially oxidizes 2-butanol having an S-configuration; or with a microorganism producing said enzyme or a crude enzyme solution prepared by disrupting said microorganism and reducing said ketone to an optically active alcohol or aldehyde to alcohol.

4. The method of claim 3, wherein the enzyme is derived from a microorganism transformed with a DNA encoding the amino acid sequence of SEQ ID NO:2.

5. A method of producing ketone or aldehyde comprising reacting alcohol with an alcohol dehydrogenase isolated from *Candida parapsilosis* having the following characteristics:
   (a) said alcohol dehydrogenase oxidizes an alcohol using $NAD^+$ as a coenzyme to produce a ketone or aldehyde;
   (b) said alcohol dehydrogenase reduces a ketone or aldehyde using NADH as a coenzyme to produce an alcohol;
   (c) said alcohol dehydrogenase has higher activity on secondary alcohols than primary alcohols; and
   (d) said alcohol dehydrogenase preferentially oxidizes 2-butanol having an S-configuration; or with a microorganism producing said enzyme or a crude enzyme solution prepared by disrupting said microorganism and oxidizing said alcohol to ketone or aldehyde.

6. The method of claim 5, wherein the enzyme is derived from a microorganism transformed with a DNA encoding the amino acid sequence of SEQ ID NO:2.

7. A method of producing an optically active alcohol comprising reacting racemic alcohol with an alcohol dehydrogenase isolated from *Candida parapsilosis* having the following characteristics:
   (a) said alcohol dehydrogenase oxidizes an alcohol using $NAD^+$ as a coenzyme to produce a ketone or aldehyde;
   (b) said alcohol dehydrogenase reduces a ketone or aldehyde using NADH as a coenzyme to produce an alcohol;
   (c) said alcohol dehydrogenase has higher activity on secondary alcohols than primary alcohols; and
   (d) said alcohol dehydrogenase preferentially oxidizes 2-butanol having an S-configuration; or with a microorganism producing said enzyme or a crude enzyme solution prepared by disrupting said microorganism and oxidizing either of the optically active isomers preferentially to isolate the remaining optically active alcohol.

8. The method of claim 7, wherein the enzyme is derived from a microorganism transformed with a DNA encoding the amino acid sequence of SEQ ID NO:2.

* * * * *